(12) United States Patent
Enderle et al.

(10) Patent No.: US 10,575,891 B2
(45) Date of Patent: Mar. 3, 2020

(54) ABLATION SYSTEM FOR LARGE-AREA SURFACE COAGULATION OF BIOLOGICAL TISSUE

(71) Applicant: Erbe Elektromedizin GmbH, Tübingen (DE)

(72) Inventors: Markus Enderle, Tübingen (DE); Klaus Fischer, Nagold (DE); Thomas Stäbler, Tübingen (DE)

(73) Assignee: Erbe Elektromedizin GmbH, Tübingen (DE)

( * ) Notice: Subject to any disclaimer, the term of this patent is extended or adjusted under 35 U.S.C. 154(b) by 438 days.

(21) Appl. No.: 15/259,965

(22) Filed: Sep. 8, 2016

(65) Prior Publication Data

US 2017/0071652 A1 Mar. 16, 2017

(30) Foreign Application Priority Data

Sep. 10, 2015 (EP) .................................... 15184689

(51) Int. Cl.
*A61B 18/04* (2006.01)
*A61B 18/00* (2006.01)

(52) U.S. Cl.
CPC .. *A61B 18/042* (2013.01); *A61B 2018/00494* (2013.01); *A61B 2018/00577* (2013.01); *A61B 2018/00607* (2013.01); *A61B 2018/00702* (2013.01); *A61B 2018/00732* (2013.01);
(Continued)

(58) Field of Classification Search
CPC ........ A61B 18/042; A61B 2018/00494; A61B 2218/005; A61B 2018/00577; A61B 2018/00982; A61B 2018/00732; A61B 2018/00767; A61B 2018/00702
See application file for complete search history.

(56) References Cited

U.S. PATENT DOCUMENTS

| 6,063,078 A * | 5/2000 | Wittkampf ......... A61B 18/1492 606/41 |
| 6,336,926 B1 | 1/2002 | Goble |
| 6,430,426 B2 | 8/2002 | Avitall |

(Continued)

FOREIGN PATENT DOCUMENTS

| CN | 1336812 A | 2/2002 |
| CN | 1874732 A | 12/2006 |

(Continued)

OTHER PUBLICATIONS

European search report in corresponding European Application No. 15184689, dated Mar. 7, 2016, 9 pages.

(Continued)

*Primary Examiner* — Jaymi E Della
*Assistant Examiner* — Rachel A. Vierra
(74) *Attorney, Agent, or Firm* — Fitch, Even, Tabin & Flannery LLP (57) ABSTRACT

The ablation system (10) according to the invention works with an ablation probe (12, 12a) that comprises two alternatingly working spark plasma electrodes (31, 32). They generate a plasma beam (47, 48) having a non-circular cross-section, which beam is to be guided—transversely with respect to the large longitudinal axis of its preferably oval cross-section—over the tissue to be ablated, in particular the mucosa (14). In doing so, it is possible to treat large-area tissue regions by means of a reliable and easily controllable procedure.

15 Claims, 4 Drawing Sheets

(52) U.S. Cl.
CPC .............. *A61B 2018/00767* (2013.01); *A61B 2018/00982* (2013.01); *A61B 2218/005* (2013.01)

(56) References Cited

U.S. PATENT DOCUMENTS

| | | | |
|---|---|---|---|
| 6,966,907 | B2* | 11/2005 | Goble .................. A61B 18/12 606/37 |
| 7,625,368 | B2 | 12/2009 | Schechter et al. |
| 7,658,738 | B2 | 2/2010 | Nobis et al. |
| 8,641,711 | B2 | 2/2014 | Kelly |
| 2001/0049509 | A1 | 12/2001 | Sekine |
| 2002/0077585 | A1 | 6/2002 | Sussman et al. |
| 2003/0028189 | A1 | 2/2003 | Woloszko et al. |
| 2003/0181900 | A1 | 9/2003 | Long |
| 2004/0215180 | A1 | 10/2004 | Starkebaum |
| 2005/0015086 | A1 | 1/2005 | Platt |
| 2005/0118350 | A1 | 6/2005 | Koulik et al. |
| 2007/0156129 | A1 | 7/2007 | Kovalcheck |
| 2008/0243114 | A1 | 10/2008 | Schnitzler |
| 2009/0069805 | A1 | 3/2009 | Fischer et al. |
| 2009/0157114 | A1 | 6/2009 | Fischer et al. |
| 2010/0114092 | A1 | 5/2010 | Eisele et al. |
| 2010/0125164 | A1 | 5/2010 | Labombard |
| 2010/0211065 | A1* | 8/2010 | Latterell ............ A61B 18/1492 606/42 |
| 2011/0184408 | A1 | 7/2011 | Konesky et al. |
| 2012/0172874 | A1 | 7/2012 | Fischer et al. |
| 2014/0257277 | A1* | 9/2014 | Woloszko ............ A61B 18/042 606/41 |

FOREIGN PATENT DOCUMENTS

| | | |
|---|---|---|
| CN | 101588765 A | 11/2009 |
| CN | 202397597 U | 8/2012 |
| DE | 10000091 A1 | 7/2001 |
| DE | 102005007769 A1 | 8/2006 |
| RU | 2419394 C2 | 5/2011 |
| WO | 9949799 A1 | 10/1999 |
| WO | 0009053 A1 | 2/2000 |
| WO | 2008090004 A1 | 7/2008 |
| WO | 2011022069 A2 | 2/2011 |

OTHER PUBLICATIONS

U.S. Office Action dated Jul. 31, 2019, issued in U.S. Appl. No. 15/261,392 (16 pages).

First Office Action of the Chinese Patent Office and Search Report dated Sep. 4, 2018, in corresponding CN Application No. 201610805223.4 (18 pages).

European Search Report dated Mar. 2, 2016, in corresponding European Application No. 15184682 (9 pages).

Russian Office Action dated Sep. 11, 2019, in corresponding Russian Application No. 2016136235, with English translation (10 pages).

* cited by examiner

Fig.9 and 100 pF, preferably 45 pF (40 pF . . . 50 pF), can be

ABLATION SYSTEM FOR LARGE-AREA SURFACE COAGULATION OF BIOLOGICAL TISSUE

RELATED APPLICATION(S)

This application claims the benefit of European Patent Application No. 15184689.6 filed Sep. 10, 2015, the contents of which are incorporated herein by reference as if fully rewritten herein.

TECHNICAL FIELD

The invention relates to an ablation system, in particular for the large-area mucosal ablation.

BACKGROUND

For the therapeutic treatment, in particular of the gastric mucosa, for example for tumor resection or also for changing the eating and weight behavior of patients, the large-area ablation and/or coagulation of sharply defined areas of the mucosa and the submucosa may be necessary, in which case the coagulation depth in the treated area should be as uniform as possible, so that the muscularis is not destroyed. Typically, therapeutic mucosal ablation is performed by means of an endoscope, wherein special probes can be used for ablation.

For example, document WO 2011/022069 A discloses an endoscope with an end cap that is to be placed on the mucosa, and an argon plasma coagulation is performed on its inside. The cap is to limit the effective region of the argon plasma coagulation.

Document U.S. Pat. No. 8,641,711 B2 describes an instrument for the ablation of tissue layers of hollow organs, wherein the instrument comprises an electrically active head with electrodes. The head is provided with an expandable element for positioning the head relative to the oppositely located tissue wall in a defined manner.

Document US 2004/0215180 A1 discloses an ablation probe with several wire-like individual electrodes projecting from the distal end of the probe, said electrodes being connected together to an electrical conductor and being supplied via the latter with electrical current from an electrical power generator, said electrical current effecting the ablation.

Document US 2003/0181900 A1 illustrates a probe for contact-coagulation with the use of several electrodes that—during operation resting against the tissue—are connected chronologically in sequence to an HF generator consistent with a specific schematic diagram.

For the simultaneous surgical treatment of biological tissue with the use of several plasma spark probes, document DE 10 2005 007 769 A1 describes a system comprising several monopolar instruments that are connected to a single HF generator via a high-voltage switch, in which case the switches are closed alternately, so that the individual instruments receive HF current intermittently.

SUMMARY

The object of the invention is to provide a concept for large-area mucosal coagulation or mucosal ablation.

The ablation system according to the invention comprises a plasma ablation probe with at least two similar spark plasma electrodes that are arranged at fixed distance from each other. They are supplied with HF voltage by a single electrical power source. This is accomplished by two electrical lines arranged parallel to each other to the spark plasma electrodes, as well as a switch arrangement provided between the source and the lines in order to alternately supply the spark plasma electrodes with HF voltage. Furthermore, the ablation system comprises a gas source and at least one fluid line that leads from the gas source to the spark plasma electrodes.

Referring to the ablation system according to the invention, at least two plasma jets are emitted by the ablation probe, said jets impinging directly next to each other on the tissue to be treated. The plasma jets are alternatingly energized (excited), i.e., the two spark plasma electrodes ignite alternatingly. The two plasma jets can combine to form a beam having a flattened oval cross-section, a strip-shaped cross-section or the like. When the plasma beam travels across the tissue in a direction transverse to its cross-section, a wide tissue strip is coagulated. Due to the intermittent firing of the sparks on the two spark plasma electrodes it is possible—on the one hand—to work at a high voltage and high current and thus with high momentary power output and it is possible—on the other hand—to limit the mean output in such a manner that the ablation depth is restricted to a desired dimension and damage to the lower-lying tissue, or even the perforation of the hollow organ to be treated, can be prevented.

The mentioned effects are noted especially when the spark plasma electrodes are arranged at an acute angle opening in distal direction and facing away from each other. In doing so, the treatment width is maximized, in which case the outside dimensions of the plasma ablation probe are kept as small as possible and, in any event, are smaller than in parallel-arranged spark plasma electrodes that would generate a comparable treatment width.

Furthermore, particularly preferred is an embodiment, wherein the ablation probe comprises two adjacent gas ejection nozzles, wherein each gas ejection nozzle contains one spark plasma electrode. Preferably, the gas ejection nozzles are arranged so as to face away from each other at an acute angle that opens in distal direction, so that the generated plasma jets diverge slightly. In conjunction with this, it is also possible to arrange the two spark plasma electrodes in a single gas ejection nozzle that may be, for example, non-circular, for example be configured elongated in the form of a slit nozzle in order to generate a fan-shaped plasma beam. Independently thereof, the ablation probe may be provided with a single fluid line for the supply of gas or also with two separate fluid lines that are disposed for their gas supply. In doing so, geometrically different structural concepts can be implemented.

The two spark plasma electrodes are supplied with a voltage by two electrical lines that are preferably arranged so that they electrically couple with each other. For example, the coupling may be capacitive, this being given in that the two electrical lines are arranged parallel to each other at a small distance, so that, between both lines (i.e., the voltage-carrying line and the potential-free line) a capacitance of at least a few Picofarad (pF), advantageously between 10 pF measured. By electrically coupling the two lines together a complete recombination of the plasma in front of the respectively switched off electrode and thus a voltage peak on this electrode during re-ignition is avoided during an ablation procedure with quick switching of the switch arrangement. This equalizes and stabilizes the operation of the ablation probe and improves the coagulation outcome.

The switch arrangement can continuously switch with a frequency between 1 and 20 Hz, preferably with a frequency of 5 Hz, so that both spark plasma electrodes are alternately connected to the HF voltage source. In doing so, one line is connected to the HF voltage source and the respectively other line is switched to no voltage (potential-free). The switch arrangement is preferably provided on the generator. As a result of the (capacitive) coupling of the two lines a low-capacitance current flows in the respective switched-off phase via the switched off spark plasma electrode, said current preventing a complete recombination of the plasma during this short phase of operation.

While the switch arrangement is being switched, the two spark plasma electrodes may be briefly connected to the HF source. The pre-ionization of the plasma on the so-far inactive electrode facilitates—during this brief phase—the resumption of the operation of the previously briefly inactive spark plasma electrode, despite the relatively low voltage due to the operation of the other electrode. If, however, switching occurs with minimal gaps, i.e., in a brief moment in which none of the electrodes is connected to the HF electrode, the previously inactive electrode will ignite slightly and without the HF voltage source generating too high a voltage peak. In doing so, the disruptive spark breakdowns that could lead to undesirable tissue damage are avoided.

Typically, the ablation probe is used endoscopically. To do so, it is preferably attached to an endoscope outside the lumen of said endoscope and held on said lumen's distal end by means of an adapter.

The endoscope and the ablation probe may be arranged in different lumina of a plastic foil tube. The endoscope remains available for another function, i.e., for other instruments, for the supply of fluids, for the visual inspection and/or for the illumination of the operating field.

Details of advantageous embodiments of the invention are the subject matter of the description, the claims and the drawings hereinafter. They show in

DETAILED DESCRIPTION

Figures 1, 2:
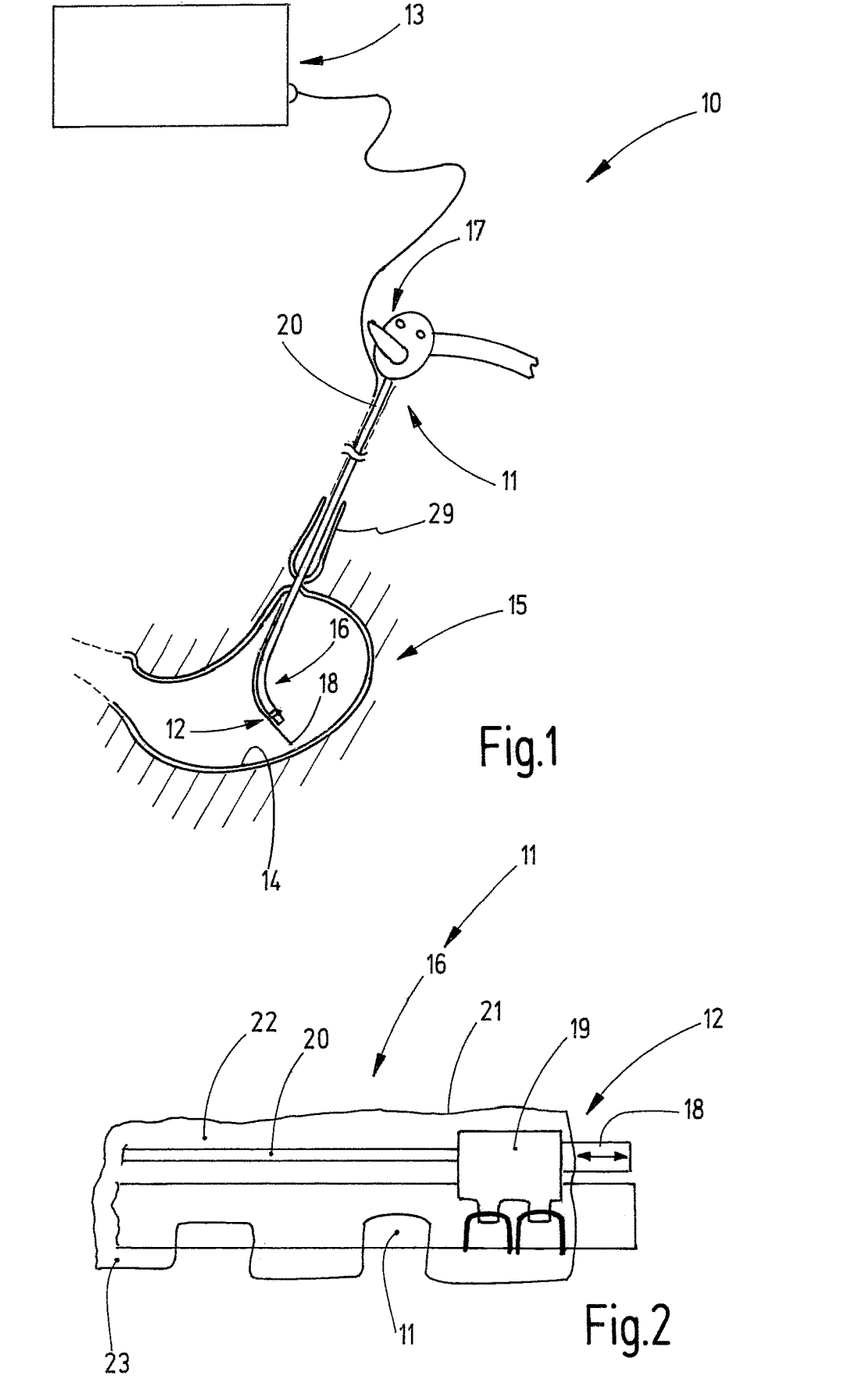
FIG. 1 a schematic illustration of an ablation system according to the invention comprising an ablation probe on an endoscope while in use.
FIG. 2 a sectional side view of the distal end of the endoscope as in FIG. 1, with the ablation probe attached.

FIG. 1 shows an ablation system 10 which comprises an endoscope 11 with an ablation probe 12 and a device 13 for providing media and operating power for the ablation probe 12 and, optionally, additional instruments. The ablation probe 12 is disposed for the treatment, in particular coagulation and/or ablation, of the inside skin of a hollow organ, in particular the mucosa 14 of a stomach 15. To accomplish this, the distal end 16 of the endoscope 11 is guided and bent by means of control elements 17 in such a manner that the ablation probe 12, in particular a head 18 provided on the distal end of said probe, is positioned advantageously at the desired distance perpendicularly with respect to the mucosa 14 and is moved along said mucosa.

Figures 3, 4, 5:
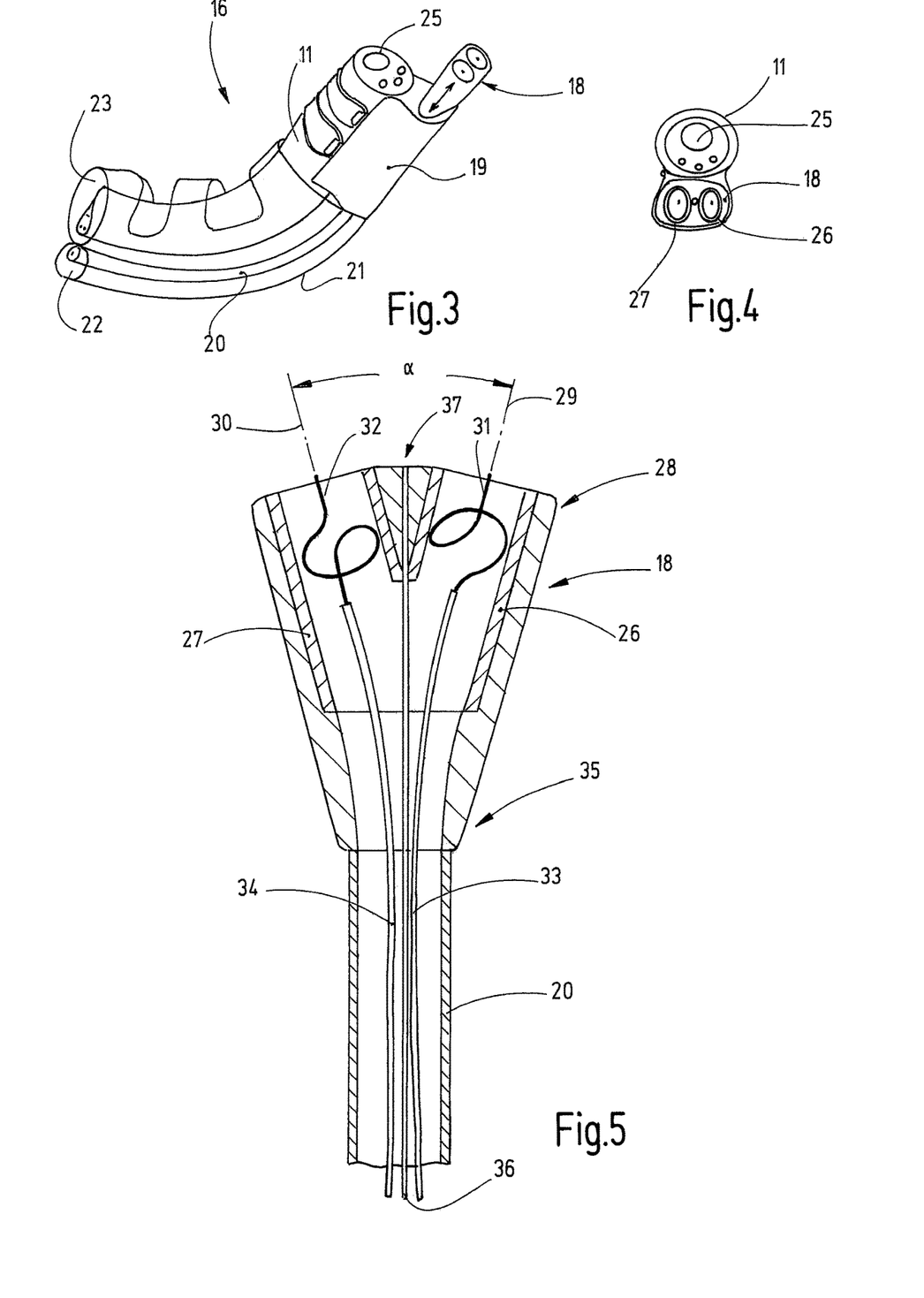
FIG. 3 a perspective view of the endoscope with the ablation probe as in FIG. 2.
FIG. 4 a front view of the endoscope and the ablation probe as in FIGS. 2 and 3.
FIG. 5 a sectional view of a detail of the ablation probe.

The distal end 16 of the endoscope 11 and the ablation probe 12 are shown separately in FIG. 2. The endoscope 11 is embodied as a single-lumen or multi-lumen tube that can be curved in a target manner by means of the control elements 17. An adapter 19 is held on the distal end 16 of the tube, said adapter being associated with the ablation probe 12. Furthermore associated with the ablation probe 12 is the head 18 that, as identified by a double-arrow in FIG. 2, can be moved in longitudinal direction of the end 16 of the endoscope 11, as well as a tube 20 displaying tensile stiffness and compression stiffness, for example a fluid line 20 that is rigidly connected to the head 18 and extends parallel to the endoscope 11. As can be inferred from FIG. 1, the tube 20 leads to the device 13. The endoscope 11 and the tube 20 can be accommodated in a tube sleeve 21, in which case the ablation probe 12 extends through a first lumen 22 of the tube sleeve 21 and the endoscope 11 extend through a second lumen 23 of the tube sleeve 21. Consequently, the total arrangement comprising the endoscope 11, the ablation probe 12 and the tube sleeve 21 can be inserted through the esophagus 14 into the stomach 15 of a patient and its movement controlled there, just like in the case of a common endoscope.

FIG. 3 illustrates the end 16 of the endoscope 11 described so far, this time in a perspective view. As is obvious, the endoscope 11 may contain one or more lumens 25 as well as image-transmission means, illumination devices and the like. As is shown in FIG. 3, the adapter 19 may be attached with suitable clamping means or other fastening means to the end of the endoscope 11. FIG. 4 allows the inference that the head 18 may have a non-circular cross-section, in which case it may be provided with two gas ejection nozzles 26, 27. They may be configured, for example, as ceramic inlays. At least on the distal end 28 of the head 18, the gas ejection nozzles 26, 27 have opening axes 29, 30 that preferably include an acute angle $\alpha$. It is preferably between 10° and 60° and is further preferably 10° to 30°, in particular essentially 25°.

Concentrically with respect to the ejection axes 29, 30 there are provided spark plasma electrodes 31, 32 that may be configured, for example, as needle-shaped or pin-shaped tungsten bodies or as otherwise electrically conductive, thermally stable elements. The spark plasma electrodes 31, 32 that are centered in the gas ejection nozzles are preferably also arranged at an cute angle of preferably 10° to 60°, preferably 10° to 30°, in particular 25°. The distance of the spark plasma electrodes 31, 32 from each other is preferably 5 mm to 10 mm, preferably 7.5 mm. The spark plasma electrodes 31, 32 may be arranged completely in the gas ejection nozzles 26, 27 or may partially project therefrom, as is shown in FIG. 5.

Each of the spark plasma electrodes 31, 32 is connected to an electrical line 33, 34, respectively, the conductors of which are provided with an electrical insulation, i.e., a dielectric. Both lines 33, 34 extend so as to run next to each other through the lumen of the tube 20 that is connected to the proximal end 35 of the head 18 for supplying the gas ejection nozzles 26, 27 with gas. The lines may be twisted together, configured as a strip line or be loosely side by side in the tube 20.

Furthermore, in the tube 20 there may be provided a fluid line 36 that is disposed to supply fluid, for example water (NaCl solution) to a fluid ejection nozzle 37 located on the distal end of the head 28. Alternatively, the fluid line 36 may also be guided outside the tube 20 along its outside. The fluid ejection nozzle 37 may be used to inject a fluid, in particular NaCl solution, under the mucosa 14 in order to lift the mucosa off the underlying tissue, in particular the submucosa 51. To accomplish this, one or more bubble-like fluid depots may be created under the mucosa 14. This may be done, e.g., prior to the application of HF current. Prior to the thermal ablation of, for example, the mucosa 42, fluid can be introduced into the stomach wall through the ejection opening 37 in such a manner that a fluid cushion forms advantageously under the desired ablation site.

Figure 6:
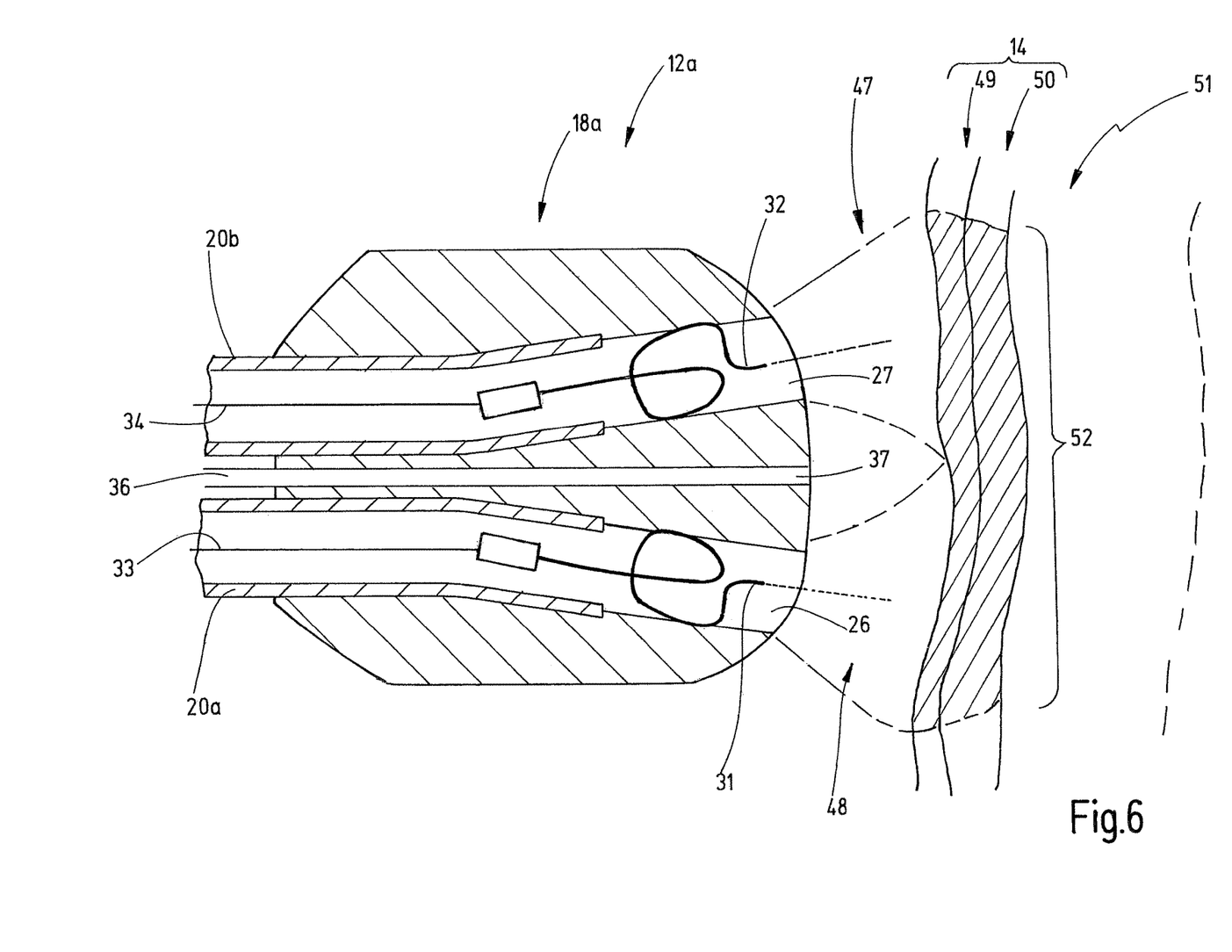
FIG. 6 a schematic representation, in longitudinal section, of a modified embodiment of an ablation probe, during the operation while acting on the mucosa.

FIG. 6 shows a modified embodiment of the ablation probe, namely ablation probe 12a. It has a head 18a whose gas ejection nozzles 26, 27 are supplied with gas by separate tubes 20a, 20b displaying tensile stiffness and compression stiffness. The spark plasma electrodes 31, 32, in turn, may project from the gas ejection nozzles 26, 27 or, as shown, be recessed therein. The electrical lines 33, 34 connected to the spark plasma electrodes 31, 32 can be insulated or, as shown, be guided as exposed conductors through the tubes 20a, 20b that are arranged parallel next to each other along the endoscope 11 and extend through the lumen 22 (FIG. 3). Other than that, the description of the ablation probe 12, together with the explanations given in conjunction with FIGS. 1 to 5, do apply.

Figures 7, 8, 9:
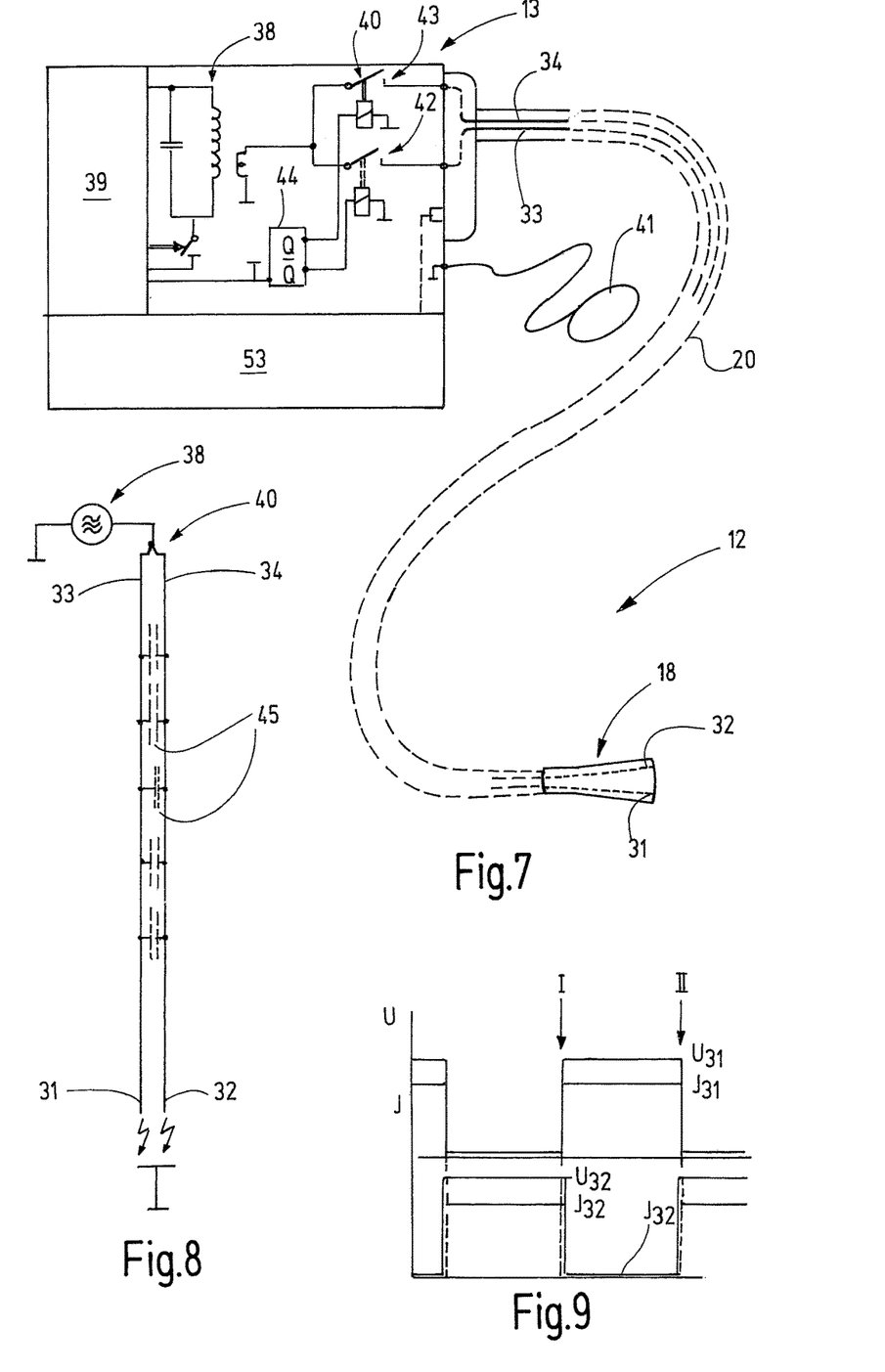
FIG. 7 an electrical circuit diagram of the ablation system.
FIG. 8 a schematized electrical representation of the ablation system.
FIG. 9 a time-dependency diagram for the schematized illustration of the operation of the switch arrangement of the ablation system as in FIGS. 7 and 8.

The device 13 that is shown in greater detail in FIG. 7 is used for the supply of the ablation probe 12. The device 13 comprises an electrical power source 38, for example an HF generator 38 that typically oscillates at a frequency between 100 kHz and one MHz, preferably at a frequency of, for example, 300 kHz to 400 kHz, in particular 350 kHz. It receives its power from a power supply and control unit 39.

High-frequency AC voltage that is uncoupled from the HF generator 38 is output via a switch arrangement 40 alternatingly to the lines 33, 34 and thus alternatingly to the spark plasma electrodes 31, 32. The switch arrangement 40 may be accommodated as part of the device 13 or in a separate intermediate module that is connected to the device 13 and to the lines 33, 34.

The HF voltage that is alternatingly applied to the lines 33, 34 has a peak value of preferably several thousand Volts (e.g., 5000 Volts) so that it is capable of igniting sparks on the spark plasma electrodes 31, 32, said sparks jumping to the oppositely located biological tissue, for example, the mucosa 14 (FIG. 6). A neutral electrode 41 is provided to return the electrical current, said electrode being connected to the device 13 and fastened to the patient over a large area.

The switch arrangement 40 comprises a first switch 42 that can connected the line 33 to the HF generator 38 and a second switch 43 that can connect the line 34 to the HF generator 38. The switches or make-contacts 42, 43 are, for example, part of a relay or two separate relays that switch inversely. For energization, a clock signal T comes from the power supply and control unit. The signal T is used by an amplifier and inverter block 44 for the inverse energization of the drives that move the switches 42, 43.

The first switch 42 and the second switch 43 work alternatingly, so that the switch 42 is open when the switch 43 is closed and vice versa. At the reversal points I, II (FIG. 9), the two switches 42, 43 may briefly both be closed or also be briefly both be open if there is a gap in operation. The time of the overlapping closure (both closed) or switching gap (none closed) is short compared to the total closing time of each pulse. The switching occurs at 1 Hz to 20 Hz, preferably at 5 Hz. The electrical lines 33, 34 extend closely adjacent through the lumen of the tube 20 (or, alternatively, through two tubes 20a, 20b, according to FIG. 6) from the device 13 to the head 18.

The electrical conditions are illustrated in FIG. 8. The parallel-guided lines 33, 34 are typically clearly longer than 1 m (for example, 2 m to 5 m). Consequently, the two lines 33, 34 couple with a capacitance greater than 1 pF, as indicated by the capacitors shown in dashed lines in FIG. 8. These are not discrete components but are to symbolize the coupling capacitance existing between two lines 33, 34. Typically, this is in the range between 1 and 200 pF and influences the operation of the ablation probe 12. The existing coupling capacitance 45 does not preclude that additional coupling elements, for example, ohmic resistors, capacitors and/or the like are arranged between two lines 33, 34.

To illustrate the operation of the ablation probe 12, reference is made to FIGS. 8 and 9 hereinafter. In doing so, it is initially assumed that the head 18 is supplied via the tube 20 with gas, e.g. argon, from a gas source 53 that may be part of the device 13 or be separate.

Furthermore, the switch arrangement 40 that switches alternatingly at a frequency of, for example, 5 Hz establishes a connection between the HF generator 38 and the line 34 in the viewed phase. Consequently, the HF voltage is applied to the spark plasma electrode 32. There forms, in front of the spark plasma electrode 32, a plasma beam 47 that widens slightly in front of the gas ejection nozzle 27 and impinges on the mucosa 14. In FIG. 9, this is symbolized by the voltage U32 and the current I32. Both are different from zero and result in a considerable power of clearly above 100 Watts.

At switching point I the switch arrangement 40 changes. Now the voltage of the generator 38 is applied to the line 33 and thus to the spark plasma electrode 31. It now forms a plasma beam 48 in front of the gas ejection nozzle 26, said beam, in turn, impinging on the biological tissue, for example, the mucosa 14. The voltage U31 is applied to the spark plasma electrode 31 and current I32 flows. Due to the capacitive coupling, however, the current I32 does not drop exactly to zero. Rather, a small portion of the coagulation current flowing in the line 33 flows across the coupling capacitor 45 to the line 32, so that a residual ionization can be maintained in the vicinity of the spark plasma electrode 32. If the switch arrangement 40 is switched again, this facilitates the renewed ignition of the spark on the spark plasma electrode 32 at time II. Consequently, it is prevented that the generator 38 must first build up an increased voltage in order to apply the breakdown voltage for the spark breakdown, and at least the requirement of such a voltage increase is minimized. With this it can thus be achieved that the energy output in the two plasma jets 47, 48 is equalized, as a result of which the user has greater control over the treatment.

As can also be inferred from FIG. 6, different layers 49, 50 of the mucosa 14 can be reliably coagulated, and underlying layers—here in particular the muscularis—can be spared. Furthermore the power distribution is relatively uniform in each plasma jet 47, 48 so that both jets together leave a wide coagulation track 52 having a width of 10 to 18 mm when the head 18, 18a is guided transversely to a line connecting the spark plasma electrodes 31, 32 (perpendicular to the plane of projection in FIG. 6) along the mucosa 14.

The ablation system 10 according to the invention works with an ablation probe 12, 12a that comprises two alternatingly working spark plasma electrodes 31, 32. They generate a plasma beam 47, 48 having a non-circular cross-section, which beam is to be guided—transversely with respect to the large longitudinal axis of its preferably oval cross-section—over the tissue to be ablated, in particular the mucosa 14. In doing so, it is possible to treat large-area tissue regions by means of a reliable and easily controllable procedure.

LIST OF REFERENCE SIGNS

| | |
|---|---|
| 10 | Ablation system |
| 11 | Endoscope |
| 12, 12a | Ablation probe |
| 13 | Device |
| 14 | Biological tissue, mucosa |
| 15 | Stomach |
| 16 | Distal end of the endoscope 11 |
| 17 | Control elements of the endoscope 11 |
| 18, 18a | Head |
| 19 | Adapter |
| 20, 20a, 20b | Tube displaying tensile stiffness and compression stiffness, fluid line |
| 21 | Tube sleeve |
| 22 | First lumen of the tube sleeve 21 |
| 23 | Second lumen of the tube sleeve 21 |
| 24 | Esophagus |
| 25 | Lumen of the endoscope 11 |
| 26, 27 | Gas ejection nozzles |
| 28 | Distal end of the head 18 |
| 29, 30 | Opening axes |
| α | Angle between the opening axes 30, 31 |
| 31, 32 | Spark plasma electrodes |
| 33, 34 | Lines |
| 35 | Proximal end of the head 18 |
| 36 | Fluid line |
| 37 | Fluid ejection nozzle |
| 38 | Electrical power source, HF generator |
| 39 | Power supply and control unit |
| 40 | Switch arrangement |
| 41 | Neutral electrode |
| 42 | First switch, make-contact |
| 43 | Second switch, make-contact |
| 44 | Inverter and amplifier module |
| T | Clock pulse |
| 45 | Coupling capacitance |
| 47, 48 | Plasma beam |
| 49, 50 | Layers of the mucosa (Lamina propria, Muscularis mucosae) |
| 51 | Tissue underlying the mucosa (submucosa) |
| 52 | Coagulation track |
| 53 | Gas source |

The invention claimed is:

1. An ablation system for large-area mucosal ablation, comprising:
   a plasma ablation probe comprising at least two spark plasma electrodes that are arranged adjacent to each other,
   a single electrical power source for high frequency voltage and two electrical lines that are parallel to each other leading to the at least two spark plasma electrodes,
   a switch arrangement arranged between the single electrical power source and the two electrical lines to alternatingly connect the two electrical lines to the single electrical power source such that the high frequency voltage is alternatingly supplied to the at least two spark plasma electrodes, and
   a gas source and at least one fluid line leading from the gas source to the at least two spark plasma electrodes;
   wherein the at least two spark plasma electrodes are arranged so as to face away from each other at an acute angle (α) that opens in a distal direction.

2. The ablation system as in claim 1, wherein the plasma ablation probe comprises two adjacent gas ejection nozzles, wherein each of the at least two spark plasma electrodes is arranged in a respective one of the two adjacent gas ejection nozzles.

3. The ablation system as in claim 2, wherein the two adjacent gas ejection nozzles are arranged so as to face away from each other at the acute angle (α) that opens in the distal direction.

4. The ablation system as in claim 1, wherein the at least one fluid line comprises a single fluid line that is provided for gas supply of the plasma ablation probe and the two electrical lines are guided through the single fluid line.

5. The ablation system as in claim 1, wherein the at least one fluid line comprises two fluid lines that are provided for gas supply of the plasma ablation probe and one of the two electrical lines, respectively, is arranged in each of the two fluid lines.

6. The ablation system as in claim 1, wherein the two electrical lines are arranged so as to be electrically coupled with each other.

7. The ablation system as in claim 1, wherein the two electrical lines are arranged so as to be capacitively coupled with each other.

8. The ablation system as in claim 1, wherein the switch arrangement comprises two make-contacts, wherein at least one of the two make-contacts is closed at any time.

9. The ablation system as in claim 1, wherein the switch arrangement is configured to switch at a frequency between 1 Hz and 20 Hz.

10. The ablation system as in claim 1, wherein the single electrical power source is configured to provide the HF voltage from 2000 V to 5000 V at a frequency from 100 kHz to 1 MHz and a power of 50 W to 200 W.

11. The ablation system as in claim 1, wherein an endoscope is provided for guiding the plasma ablation probe.

12. The ablation system as in claim 11, wherein the endoscope has at least one lumen and the plasma ablation probe is guided on the endoscope outside the at least one lumen of said endoscope.

13. The ablation system as in claim 11, wherein the plasma ablation probe is held on the endoscope by an adapter.

14. The ablation system as in claim 11, wherein the endoscope and the plasma ablation probe are arranged in different lumina of a tube sleeve.

15. An ablation system, in particular for large-area mucosal ablation, comprising:
   a plasma ablation probe comprising at least two spark plasma electrodes that are arranged adjacent to each other,
   a single electrical power source for high frequency voltage and two electrical lines that are parallel to each other leading to the at least two spark plasma electrodes,
   a switch arrangement arranged between the single electrical power source and the two electrical lines to alternatingly connect the two electrical lines to the single electrical power source such that the high frequency voltage is alternatingly supplied to the at least two spark plasma electrodes, and a gas source and at least one fluid line leading from the gas source to the at least two spark plasma electrodes;

wherein the plasma ablation probe comprises two adjacent gas ejection nozzles, wherein each of the at least two spark plasma electrodes is arranged in a respective one of the two adjacent gas ejection nozzle; and wherein the two adjacent gas ejection nozzles are arranged so as to face away from each other at an acute angle ($\alpha$) that opens in a distal direction.

* * * * *